(12) United States Patent
Marom et al.

(10) Patent No.: US 8,975,244 B2
(45) Date of Patent: Mar. 10, 2015

(54) PROCESS AND INTERMEDIATES FOR THE PREPARATION OF ABIRATERONE ACETATE

(71) Applicant: Mapi Pharma Ltd., Ness Ziona (IL)

(72) Inventors: Ehud Marom, Kfar Saba (IL); Shai Rubnov, Tel Aviv (IL); Michael Mizhiritskii, Rehovot (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 14/176,463

(22) Filed: Feb. 10, 2014

(65) Prior Publication Data

US 2014/0155363 A1    Jun. 5, 2014

Related U.S. Application Data

(63) Continuation of application No. PCT/IL2013/050621, filed on Jul. 22, 2013.

(60) Provisional application No. 61/675,349, filed on Jul. 25, 2012.

(51) Int. Cl.
*C07D 211/68* (2006.01)
*A61K 31/58* (2006.01)
*C07J 43/00* (2006.01)

(52) U.S. Cl.
CPC ............... *C07J 43/003* (2013.01); *C07J 43/00* (2013.01); *A61K 31/58* (2013.01)
USPC .......................................... 514/176; 546/285

(58) Field of Classification Search
None
See application file for complete search history.

(56) References Cited

U.S. PATENT DOCUMENTS

| 5,604,213 | A | * | 2/1997 | Barrie et al. ................... 514/176 |
| 2005/0282825 | A1 | | 12/2005 | Malamas |

FOREIGN PATENT DOCUMENTS

| DE | 3832349 A1 | 3/1990 |
| EP | 1759765 A1 | 3/2007 |
| FR | 2811988 A1 | 1/2002 |
| WO | 2006/021777 A1 | 3/2006 |
| WO | WO 2006021777 A1 * | 3/2006 |
| WO | 2009/070869 A1 | 6/2009 |

OTHER PUBLICATIONS

Casreact 105:133724.*
Barton, D. H. R. et al., (1962) A new reaction of hydrazones. J Chem Soc 1962:470-476.
Barton, D. H. R. et al., (1983) An Improved preparations of vinyl iodides. Tetrahedron Letters 24(15):1605-1606.
Barton, D. H. R. et al., (1988) Studies on the oxidation of hydrazones with iodine and with phenylselenenyl bromide in the presence of strong organic bases; an improved procedure for the synthesis of vinyl iodides and phenyl-vinyl selenides. Tetrahedron 44(1):147-162.
Cai, D. et al., (2002) Effective lithiation of 3-bromopyridine: Synthesis of 3-pyridine boronic acid and variously 3-substituted pyridines. Tetrahedron Letters 43(23):4285-4287.
Gros, P. C. and Elaachbouni, F. (2008) Bromine-lithium exchange under non-cryogenic conditions: TMSCH2LI-LIDMAE promoted C-2 lithiation of 2,3-dibromopyridine. Chem Commun (Camb). 39:4813-4815.
Hamura et al., (2003) Synthesis of functionalized biaryl compounds via ring expansion of Alkenylcyclobutenones. Tetrahedron Letters 44(1): 167-170.
Moon, S. et al., (1990) Synthesis of dehydro-oogoniol and oogoniol: the adrenosterone route. Tetrahedron 48(7):2287-2306.
Morais, C.A. and Ciminelli, V. S. T. (2004) Process development for the recovery of high-grade lanthanum by solvent extraction. Hydrometallurgy 73(3-4):237-244.
Rani, N. et al., (2009) Bis(3-pyridyl)methylvinylsilane (L1) and 1,2-di(3-quinolyl) dimethyl disilane (L2): Synthesis and complexation reactions. Anion controlled solid state structures of cationic Ag(I)-L1 complex. Journal of Organometallic Chemistry 694(15):2442-2447.
Paradies, H. H. and Gorbing, M. (1969) A New Method for the Preparation of Organomagnesium Compounds of Pyridine. Angew Chem Internat Edit 8(4):279.
Potter, G. A. et al., (1995) Novel steroidal inhibitors of human cytochrome P45017 alpha (17 alpha-hydroxylase-C17,20-lyase): potential agents for the treatment of prostatic cancer. J Med Chem 38(13):2463-2471.
Potter, G. A. et al., (1997) A Convenient, large-scale synthesis of abiraterone acetate [3β-acetoxy-17-(3-pyridyl)androsta-5,16-diene], a potential new drug for the treatment of prostate cancer. Organic Preparations and Procedures International: The New Journal of Organic Synthesis 29(1):123-128.
Wicha, Jerzy adn Masnyk, Marek (1985) Cardiotonic steriods. Part 8, "Synthesis of 17b-(3'pyridyl)-14b-androst-4-ene-3b, 14-diol from 17 oxanedrostane derivatives" Bulletin of the Polish Academy of Sciences, Chemistry 33(1-2):19-27 (abstract).

* cited by examiner

*Primary Examiner* — Heidi Reese
(74) *Attorney, Agent, or Firm* — Rothwell, Figg, Ernst & Manbeck, P.C.

(57) ABSTRACT

The present invention relates to a process for the synthesis of (3beta)17-(3-pyridinyl)androsta-5,16-dien-3-yl acetate (Abiraterone acetate) represented by the structure of formula (1), and salts thereof, especially salts with pharmaceutically acceptable acids. The present invention further relates to certain intermediates in such processes.

18 Claims, No Drawings

PROCESS AND INTERMEDIATES FOR THE PREPARATION OF ABIRATERONE ACETATE

CROSS REFERENCE TO RELATED APPLICATIONS

The present application is a continuation application of International Application No.: PCT/IL2013/050621, with an international filing date of Jul. 22, 2013, which claims the benefit of U.S. Provisional Application No. 61/675,349 filed Jul. 25, 2012, which are incorporated herein in their entireties.

FIELD OF THE INVENTION

The present invention relates to processes for the preparation of Abiraterone acetate and salts thereof with physiologically acceptable acids. The present invention further relates to certain intermediates formed in such processes.

BACKGROUND OF THE INVENTION

Abiraterone ((3β)-17-(pyridin-3-yl)androsta-5,16-dien-3-ol) is a drug used in the treatment of patients with castration-resistant prostate cancer (CRPC). It is formulated as its prodrug—Abiraterone acetate ((3β)17-(3-pyridinyl)androsta-5, 16-dien-3-yl acetate) and sold under the brand name Zytiga. Zytiga in combination with prednisone is indicated for the treatment of patients with metastatic CRPC who have received prior chemotherapy containing docetaxel.

U.S. Pat. No. 5,604,213 discloses a method for preparation of Abiraterone acetate by palladium-catalyzed cross-coupling of steroidal 17-enol triflate (2) with a suitable pyridyl-containing nucleophilic coupling partner (Scheme 1):

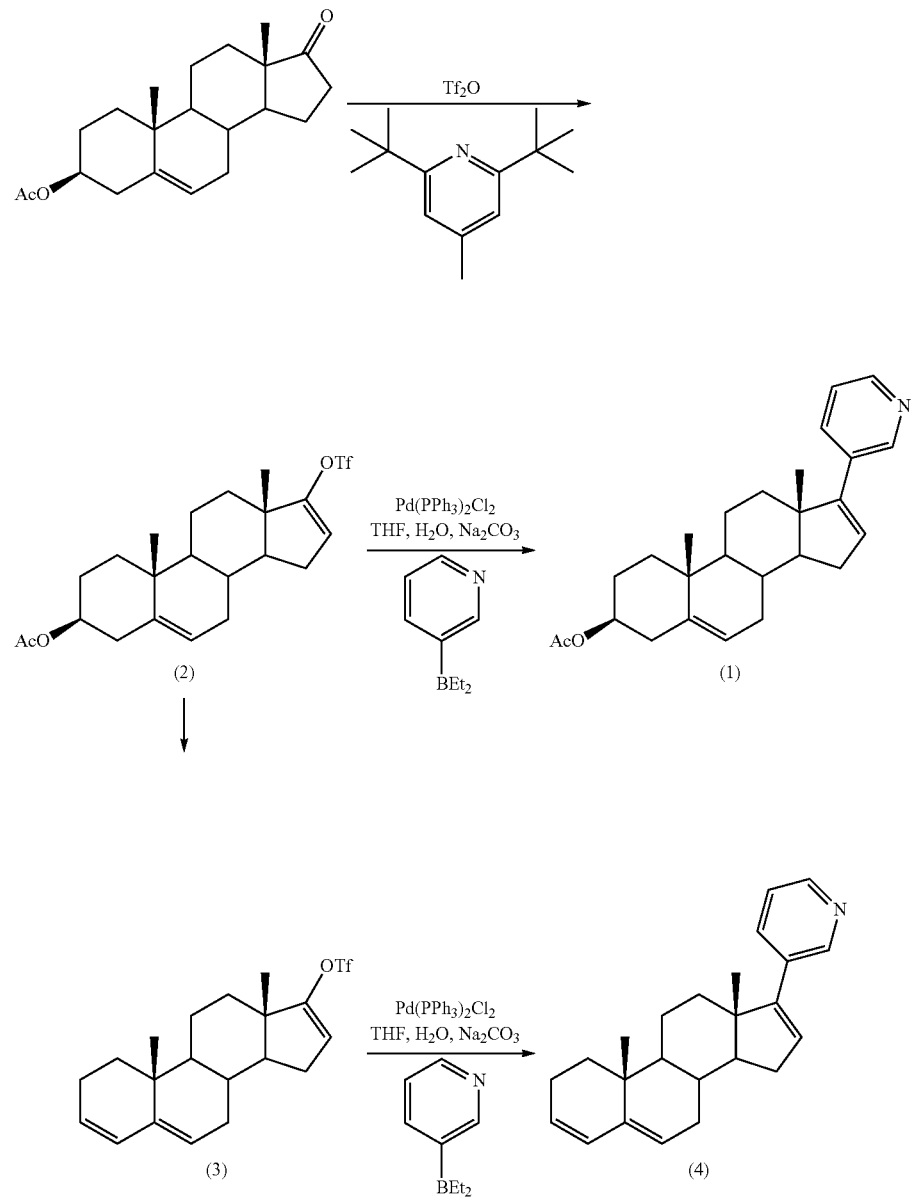

Scheme 1

According to U.S. Pat. No. 5,604,213, dehydroepiandrosterone 3-acetate was converted into its 17-enol triflate (2) by a base-catalyzed reaction with triflic anhydride in the presence of the hindered base 2,6-di-tert-butyl-4-methylpyridine. This reaction also produced the by-product 3,5-diene (3) in 10% yield. The 3-pyridyl group was then introduced into the 17-position by reacting (2) with diethyl(3-pyridyl)borane in THF, using bis(triphenylphosphine) palladium(II) chloride as a catalyst (0.01 equiv) and aqueous Na₂CO₃ as a nucleophilic activator to give the acetate (1) in 84% isolated yield. If (3) was not removed from the reaction mixture, the 3-pyridyl derivative (4) was similarly obtained. The acetyl group of (2) was reportedly stable to the mildly basic conditions of the coupling reaction (U.S. Pat. No. 5,604,213; Potter G A et al., *J. Med. Chem.* (1995), 38, 2463-2471).

Potter et al. (1995) found that the catalyst Pd(PPh₃)₂Cl₂ was superior to Pd(PPh₃)₄ and consistently gave better yields of the coupled product. The catalyst could also be used at much lower levels, and reportedly even at 0.001 equiv, good yields were obtained with prolonged reaction times. Of importance was that this reaction did not require anhydrous conditions, and indeed an aqueous THF solvent system was employed.

Nevertheless, this procedure has several potential drawbacks as a method for large-scale synthesis. Aside from the use of the expensive and noxious triflic anhydride, the formation of the enol triflate requires use of the costly hindered base 2,6-di-tert-butyl-4-methylpyridine. Furthermore, the reaction was accompanied by some elimination of acetic acid to give androsta-3,5,16-trien-17-yl triflate which required chromatographic separation from the desired product, and contributed to reducing the isolated yield of the 3-acetate of dehydroepiandrosterone to a moderate 58%. These problems prompted consideration of an alternative steroidal precursor suitable for the cross-coupling reaction.

U.S. Pat. No. 5,604,213 and Potter, G A et al. *Organic Preparations and Procedures International: The New Journal for Organic Synthesis* (1997), 29:1, 123-128, disclose another method for Abiraterone acetate synthesis based on steroidal vinyl halides such as iodide (6) (Scheme 2):

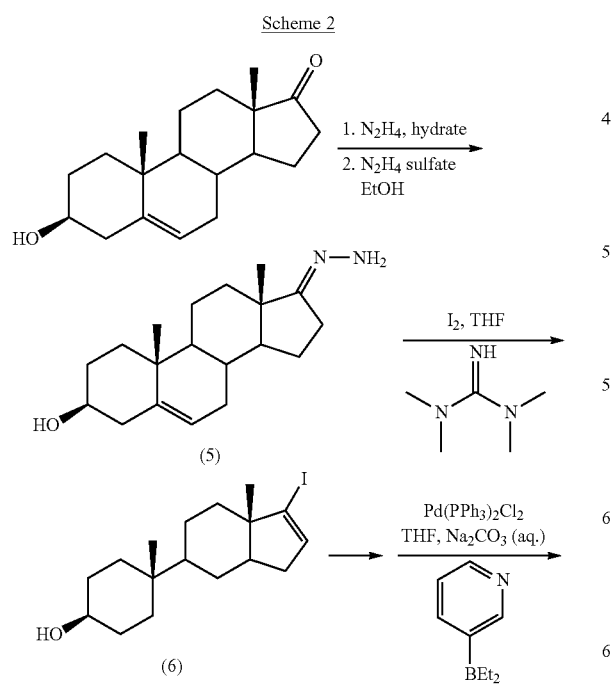

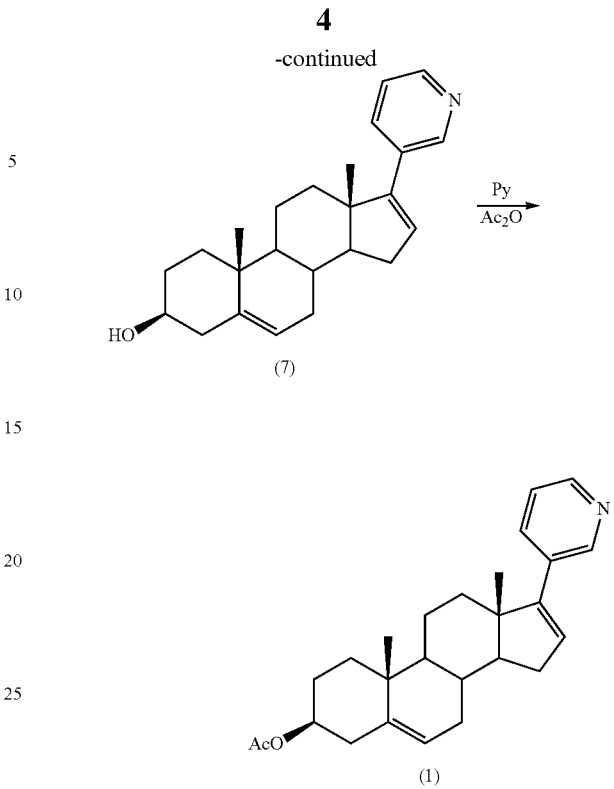

Such steroidal vinyl iodides (6) are easily obtained from the corresponding 17-hydrazones (D. H. R. Barton, et al. *J. Chem. Soc.*, (1962), 470; D. H. R. Barton, et al. *Tetrahedron Lett.* (1983), 24, 1605; Derek H. R. Barton, et al. *Tetrahedron* (1988), 44, 147).

The palladium catalyzed cross-coupling reaction of (6) with diethyl(3-pyridyl) borane conveniently proceeded without the need to protect the 3-hydroxyl function to give (7), whereas the use of an enol triflate in the coupling reaction does not allow this option. However, coupling with the iodide was much slower, requiring 4 days at 80° as compared with the 1 hr required when an enol triflate precursor was used. Moreover, the prolonged reaction time required for the cross-coupling reaction using the vinyl iodide (6) had enabled a Heck-type reaction to occur between the initial product (7) and the bis(triphenylphosphine)-palladium derivative of (6) to form by-product (8) and its acetylated form (9), which can be separated from Abiraterone only by reverse phase chromatography (Potter et al. 1997) (Scheme 3).

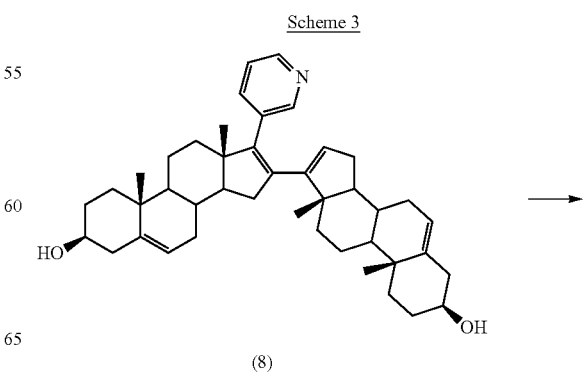

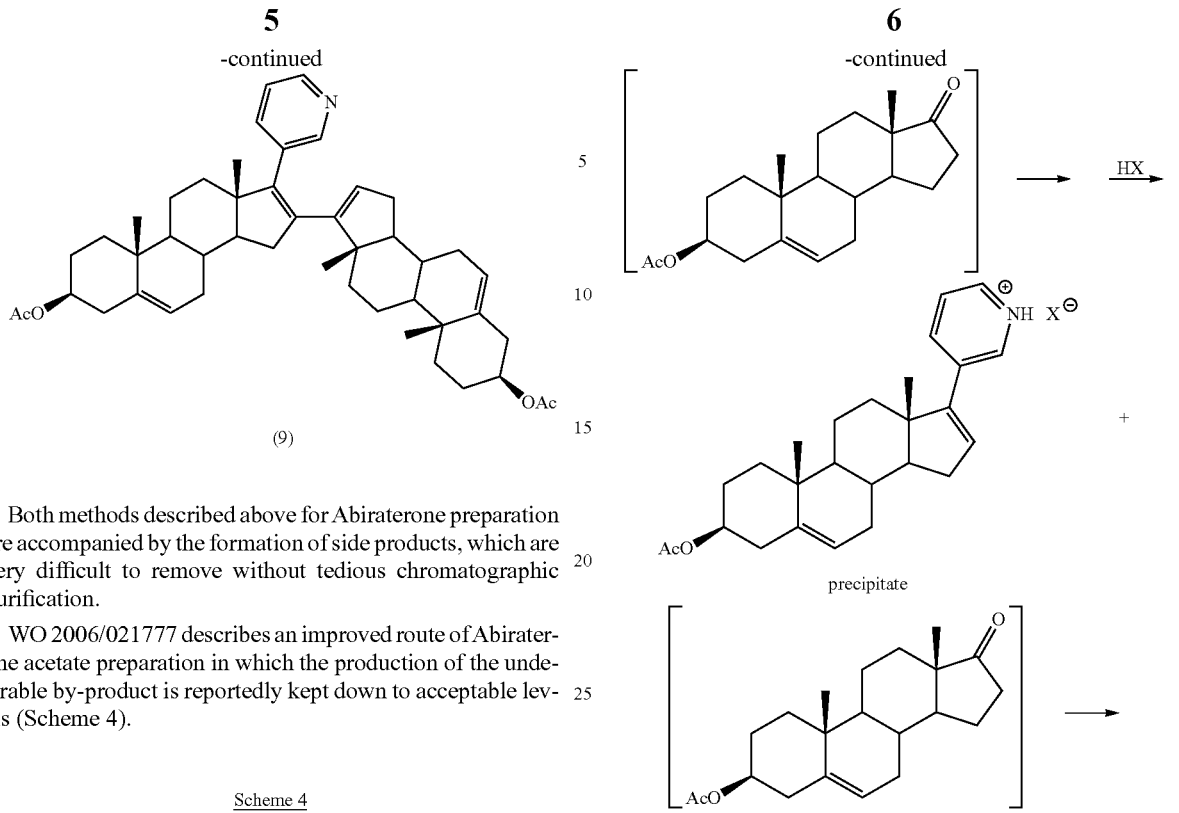

Both methods described above for Abiraterone preparation are accompanied by the formation of side products, which are very difficult to remove without tedious chromatographic purification.

WO 2006/021777 describes an improved route of Abiraterone acetate preparation in which the production of the undesirable by-product is reportedly kept down to acceptable levels (Scheme 4).

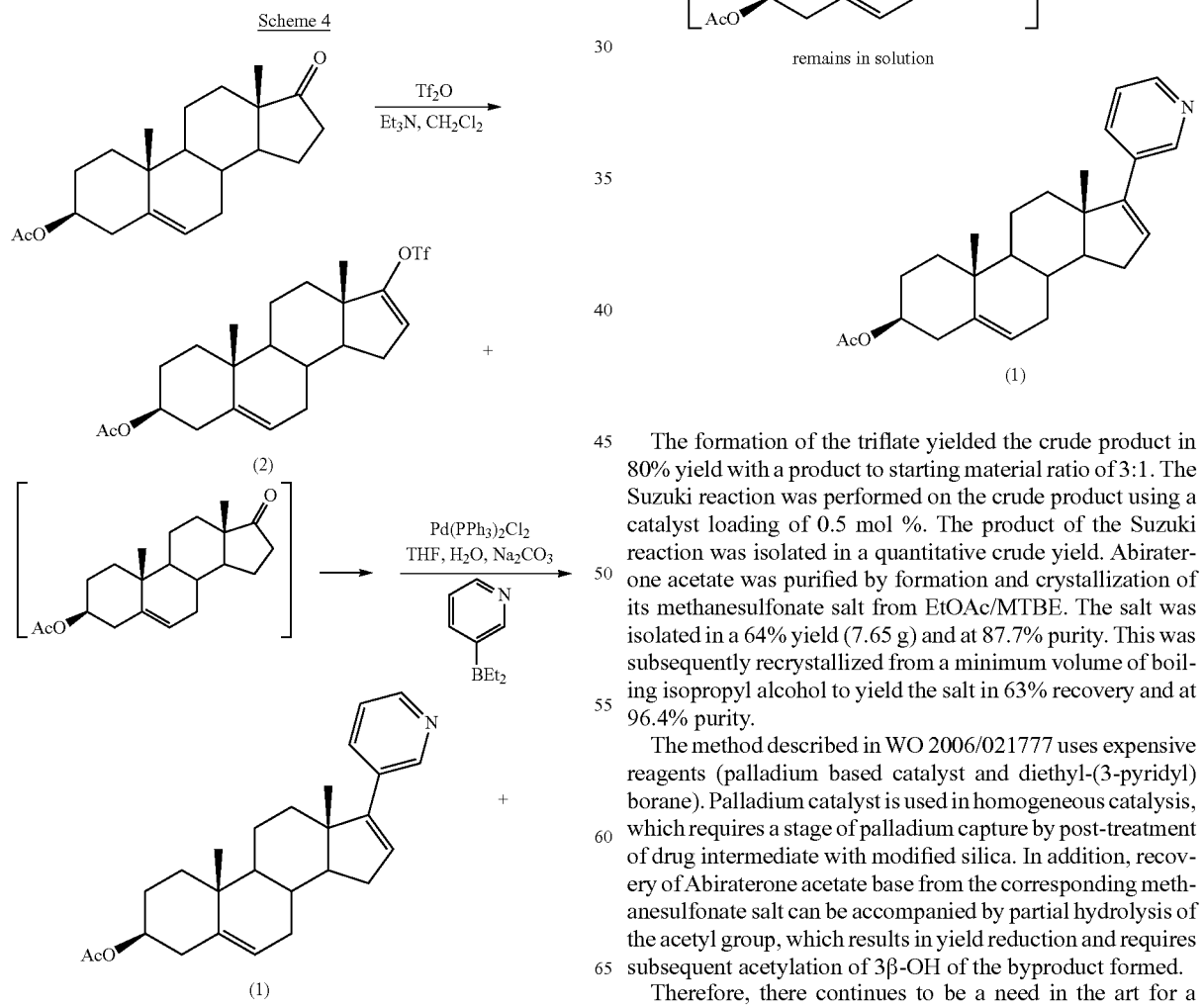

The formation of the triflate yielded the crude product in 80% yield with a product to starting material ratio of 3:1. The Suzuki reaction was performed on the crude product using a catalyst loading of 0.5 mol %. The product of the Suzuki reaction was isolated in a quantitative crude yield. Abiraterone acetate was purified by formation and crystallization of its methanesulfonate salt from EtOAc/MTBE. The salt was isolated in a 64% yield (7.65 g) and at 87.7% purity. This was subsequently recrystallized from a minimum volume of boiling isopropyl alcohol to yield the salt in 63% recovery and at 96.4% purity.

The method described in WO 2006/021777 uses expensive reagents (palladium based catalyst and diethyl-(3-pyridyl)borane). Palladium catalyst is used in homogeneous catalysis, which requires a stage of palladium capture by post-treatment of drug intermediate with modified silica. In addition, recovery of Abiraterone acetate base from the corresponding methanesulfonate salt can be accompanied by partial hydrolysis of the acetyl group, which results in yield reduction and requires subsequent acetylation of 3β-OH of the byproduct formed.

Therefore, there continues to be a need in the art for a practical method for making Abiraterone acetate, which not only avoids the problems of the existing art, but is also safe, cost effective, and industrially feasible.

SUMMARY OF THE INVENTION

The present invention relates to a process for the synthesis of (3β)17-(3-pyridinyl)androsta-5,16-dien-3-yl acetate (Abiraterone acetate) represented by the structure of formula (1), and salts thereof, especially salts with pharmaceutically acceptable acids. The present invention further relates to certain intermediates in such processes.

The process of the invention is unexpectedly advantageous over the processes described in the prior art (e.g. U.S. Pat. No. 5,604,213; WO 20060/21777). The mild reaction conditions, availability and low cost reagents make this approach industrially useful for Abiraterone acetate production.

The process of the present invention comprises the following steps (Scheme 5):

a). coupling a protected dehydroepiandrosterone (10) with a pyridinyl derivative (11) to form a pyridinyl hydroxy derivative (12);

b). dehydration of compound (12) to form (17-pyridin-3-yl)-androsta-5,16-diene (13); and c). transformation of compound (13) into (3β)17-(3-pyridinyl)androsta-5,16-dien-3-yl acetate (Abiraterone acetate) (1).

Scheme 5

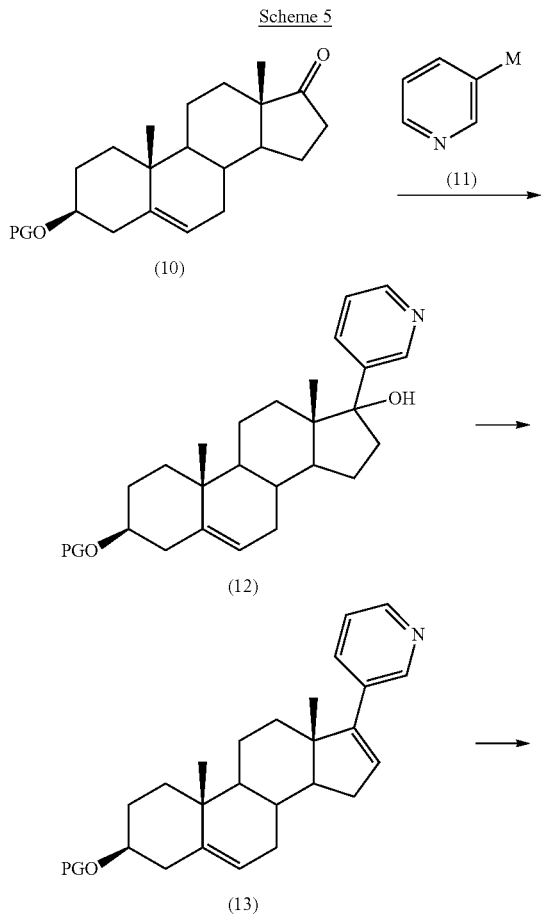

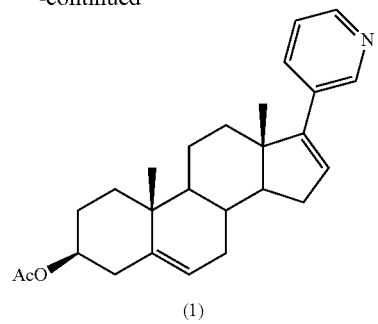

(1)

wherein
PG is a hydroxyl protecting group; and
M is selected from the group consisting of Li, Na, K, MgX, ZnX, CdX, Si(R)$_3$,
Ge(R)$_3$ and Sn(R)$_3$); wherein X is a halogen and R is a substituted or unsubstituted alkyl, cycloalkyl, alkylaryl or aryl.

In some preferred embodiments, M is Li. In other preferred embodiments, M is MgX wherein X is Cl, Br or I.

It is apparent to a person of skill in the art that the configuration of the Abiraterone acetate scaffold is as follows:

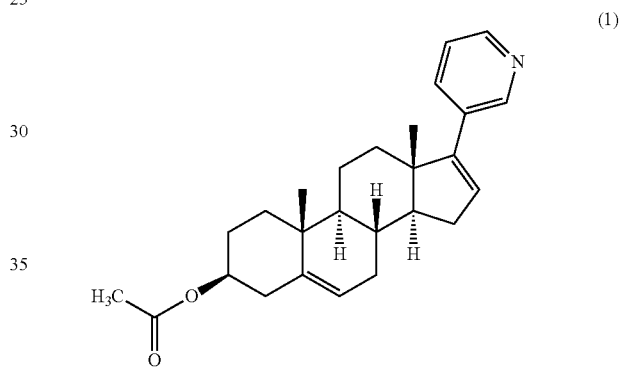

(1)

The same configuration is applicable to the Abiraterone acetate intermediates disclosed herein.

The hydroxyl protecting group can be any protecting group known in the art, and is preferably selected from the group consisting of acetate (Ac), benzyl (Bzl), Si(R$^a$)$_3$, tetrahydropyranyl (THP) and trityl (Trt), wherein R$^a$ is a substituted or unsubstituted alkyl, cycloalkyl, alkylaryl or aryl. In some preferred embodiments, the hydroxyl protecting group PG is benzyl (Bzl), Si(R$^a$)$_3$, tetrahydropyranyl (THP) or trityl (Trt). In additional preferred embodiments, the hydroxyl protecting group PG is Si(R$^a$)$_3$.

In one embodiment, pyridinylmetal derivative (11) is 3-pyridinyllithium (i.e., M=Li in compound 11). In accordance with this embodiment, dehydroepiandrosterone (10) may be protected by any group commonly used for protection of a hydroxyl function, excluding carbonyl containing protecting groups, and then reacted with 3-pyridyinyllithium to form pyridinyl hydroxy derivative (12).

In another embodiment, pyridinylmetal derivative (11) is a 3-pyridinylmagnesium halide of general formula 3-PyMgX (i.e., M=MgX in compound 11), wherein X is a halogen selected from Cl, Br and I. In accordance with this embodiment, dehydroepiandrosterone (10) is may be protected by any group, commonly used for protection of a hydroxyl function, including carbonyl containing protecting groups, and then reacted with 3-pyridinylmagnesium halide to form pyridinyl hydroxy derivative (12).

Dehydration of alcohol (12) to compound (13) may be carried out directly or by conversion of hydroxyl function into a better leaving group, with each possibility representing a separate embodiment of the present invention (Scheme 6).

Scheme 6

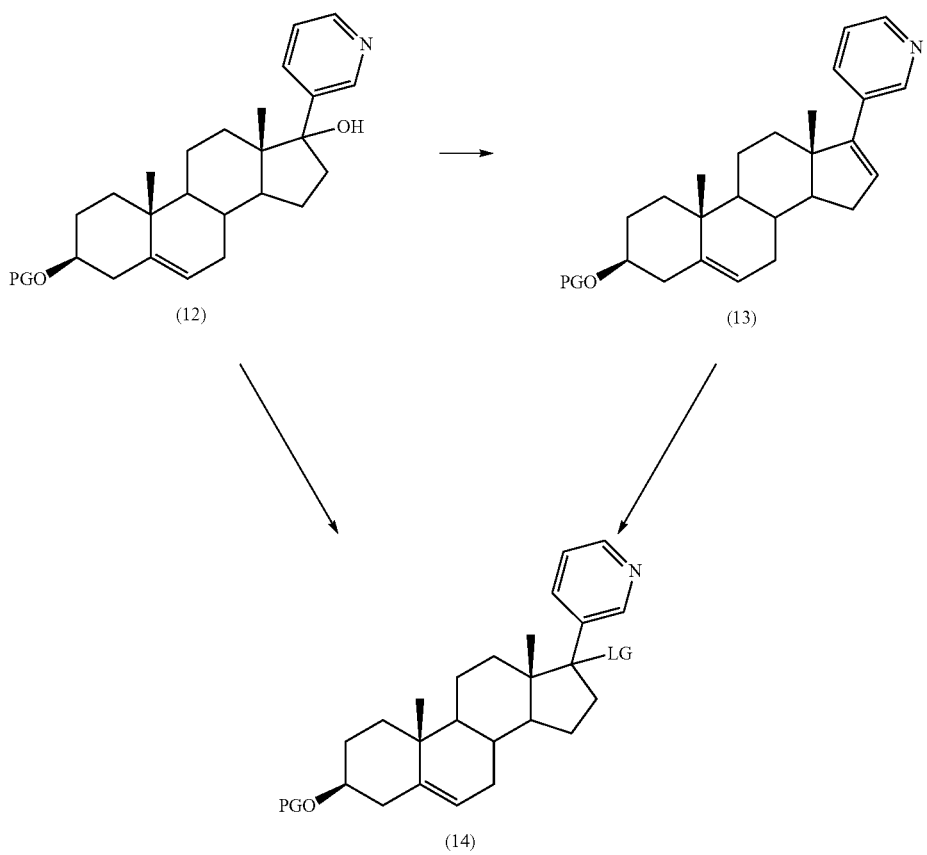

wherein LG is a leaving group, preferably a halogen or a sulfonate ester group of the formula —OSO$_2$R$^b$ wherein R$^b$ is a substituted or unsubstituted alkyl, cycloalkyl, alkylaryl or aryl. Preferred leaving groups are halogens (e.g., Cl, Br, I) or a sulfonate such as mesylate (OMs) or tosylate (OTs). Each possibility represents a separate embodiment of the present invention.

In any of the aforementioned embodiments, the step of converting compound (12) to compound (13) can be performed by any manner known in the art. Acid catalyzed dehydration is one preferred method for this step.

In another embodiment, the present invention relates to a general process for coupling ketones or aldehydes with a pyridinyl-metal derivative (11), the process comprising the step of reacting a ketone or aldehyde of the general formula (C) to a form pyridinyl-tertiary alcohol (A) (Scheme 7):

Scheme 7

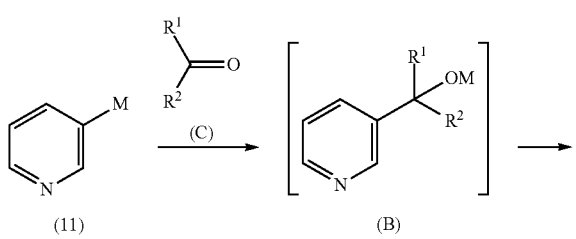

-continued

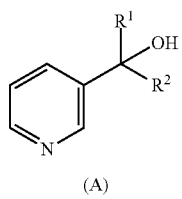

(A)

wherein R$^1$ and R$^2$ are each H or an unsubsituted or substituted alkyl, cycloalkyl, alkylaryl or aryl; and M is selected from the group consisting of Li, Na, K, MgX, ZnX, CdX, Si(R)$_3$, Ge(R)$_3$ and Sn(R)$_3$; wherein X is a halogen and R is a substituted or unsubstituted alkyl, cycloalkyl, alkylaryl or aryl.

The intermediate B may form in-situ in the process of Scheme 7, or it may be isolated if desired.

The present invention further relates to certain intermediates formed in the aforementioned processes. One novel intermediate is a compound of general formula (12)

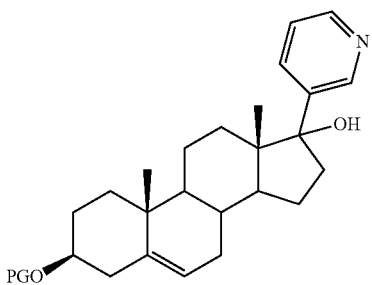

(12)

wherein PG is a hydroxy protecting group as described above.

In another embodiment, the present invention relates to an intermediate compound represented by the structure of formula (14)

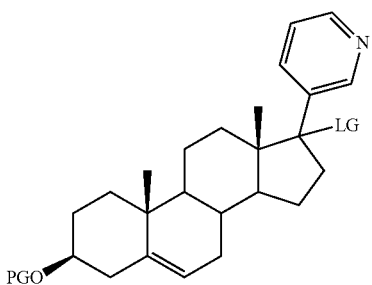

(14)

wherein PG is a hydroxyl protecting group as described above, and LG is a leaving group as described above.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to a process for the synthesis and isolation of Abiraterone acetate represented by the structure of formula (1), and salts thereof, especially salts with pharmaceutically acceptable acids. The process of the invention may further be used to prepare compounds of general formula (A) as described herein.

Chemical Definitions

The term "alkyl" as used herein alone or as part of another group refers to any saturated aliphatic hydrocarbon, including straight-chain, and branched-chain. In one embodiment, the alkyl group has 1-6 carbons designated here as $C_{1-6}$-alkyl. In another embodiment, the alkyl group has 1-4 carbons designated here as $C_{1-4}$-alkyl. Examples of alkyl groups include methyl, ethyl, n-propyl, isopropyl, n-butyl, sec-butyl, isobutyl, t-butyl, n-pentyl, 2-pentyl, 3-pentyl, 1-hexyl, 2-hexyl, 3-hexyl and the like. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention.

The term "cycloalkyl" group as used herein alone or as part of another group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

The term "aryl" as used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "alkylaryl" as used herein alone or as part of another group refers to an alkyl group as defined herein, bonded to an aryl group as defined herein. Linkage to the rest of the molecule is typically through the alkyl group.

The term "leaving group" (LG) as used herein refers to a molecular fragment that departs with a pair of electrons in heterolytic bond cleavage. Leaving groups can be anionic or neutral molecules. Suitable anionic leaving groups include, but are not limited to, halogen (F, Cl, Br, I) or an organosulfonyloxy radical of the formula —$OSO_2R^b$ wherein $R^b$ is an unsubstituted or substituted alkyl, cycloalkyl, alkylaryl or aryl (e.g., OMs (mesylate), OTs (tosylate) or OTf (triflate)). Another example of a leaving group is a moiety of formula OR' wherein R' can be any hydroxy protecting group as defined above. Suitable neutral molecule leaving groups are water ($H_2O$), and ammonia. In general, more highly stabilized anions act as better leaving groups. Each possibility represents a separate embodiment of the present invention.

As used herein, the term "OH protecting group" or "hydroxyl protecting group" (PG) refers to a readily cleavable groups bonded to hydroxyl groups. The hydroxyl protecting group can be an acid labile protecting group, a base labile protecting group, or a protecting group that is removable under neutral conditions. The nature of the hydroxy-protecting groups is not critical so long as the derivatized hydroxyl group is stable. An example of a hydroxy protecting group is an acyl group (COR wherein R=alkyl, aryl, etc.), such as an acetyl group (Ac). Another example of a hydroxy protecting group is a silyl group, which can be substituted with alkyl (trialkylsilyl), with an aryl (triarylsilyl) or a combination thereof (e.g., dialkylphenylsilyl). Examples include, but are not limited to, trimethylsilyl (TMS), triethylsilyl (TES), triisopropylsilyl (TIPS), t-butyldimethylsilyl (TBDMS), t-butyldiphenylsilyl (TBDPS), triphenylsilyl (TPS), and diphenylmethylsilyl (DPMS). A preferred example of a silyl protecting group is trimethylsilyl (TMS) or di-t-butyldimethyl silyl (TBDMS). Other examples of hydroxy protecting groups include, for example, $C_1$-$C_4$ alkyl (e.g., methyl, ethyl, propyl, butyl and the like), —$CH_2Ph$ (benzyl or bzl), allyl (All), (allyl)-CO—($C_1$-$C_6$ alkyl), —$SO_2$—($C_1$-$C_6$ alkyl), —$SO_2$-aryl, —CO—Ar in which Ar is an aryl group as defined above, —CO—($C_1$-$C_6$ alkyl)Ar (e.g., a carboxybenzyl group—"cbz"); substituted methyl ethers such as methoxymethyl (MOM), benzyloxymethyl (BOM), t-butoxymethyl, siloxymethyl, 2-cyanoethoxymethyl (CEM), tetrahydropyranyl (THP), trityl (Trt); substituted ethyl ethers such as t-butyl (t-Bu), esters such as formate, trifluoroacetate; and carbonates such as 9-fluorenylmethyl (Fmoc), and t-Butyl (Boc). Specific examples of acid sensitive protecting groups are tetrahydropyranyl (THP), methoxymethyl (MOM), tert-butyldimethylsilyl (TBDMS) and triphenylmethyl (Trityl). Each possibility represents a separate embodiment of the present invention.

Other examples of hydroxyl-protecting groups are described by C. B. Reese and E. Haslam, "Protective Groups in Organic Chemistry," J. G. W. McOmie, Ed., Plenum Press, New York, N.Y., 1973, Chapters 3 and 4, respectively; T. W. Greene and P. G. M. Wuts, "Protective Groups in Organic Synthesis," 2nd ed., John Wiley and Sons, New York, N.Y., 1991, Chapters 2 and 3 pp. 473; and Kocienski, Philip J. Protecting Groups. 3rd Ed. 2005, (2005), pp. 679. The contents of each of these references is incorporated herein by reference.

It is understood when the compound of formula (11) is 3-pyridnyllithium, the hydroxyl protecting group excludes carbonyl containing protecting group. When the compound of formula (11) is 3-pyridinylmagnesium halide, any hydroxyl protecting group, including carbonyl containing protecting groups, may be used.

The term "pharmaceutically acceptable salt" refers to an acid addition salt wherein the acid is an organic or inorganic acid. The acid addition salts include, but are not limited to, salts derived from hydrochloric, hydrobromic, hydrofluoric, trifluoroacetic, sulfuric, phosphoric, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the present invention.

The term "insertion reaction" as used herein refers to a chemical reaction where one chemical entity (a molecule or molecular fragment, such as C-D) interposes itself into an existing bond A-B of typically a second chemical entity e.g.:

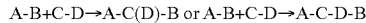

A-B+C-D→A-C(D)-B or A-B+C-D→A-C-D-B

All references cited herein are hereby incorporated by reference in their entirety, as if fully set forth herein.

DESCRIPTION OF PREFERRED EMBODIMENTS

Several non-limiting embodiments of the present invention will now be presented.

Step (a):

As contemplated herein, the applicants have found a new process, by which Abiraterone acetate of formula (1) may be prepared on a manufacturing scale from the compound of formula (10) in accordance with the process set forth in Scheme 5.

Thus, in one embodiment, the present invention relates to a process for preparing an intermediate of formula (12), comprising the step of reacting a ketone of formula (10) with 3-pyridinyl reagent (11) of general formula 3-Py-M (wherein "Py" designates pyridyl), wherein M is selected from the group consisting of Li, Na, K, MgX, ZnX, CdX, Si(R)$_3$, Ge(R)$_3$ and Sn(R)$_3$; wherein X is a halogen and R is a substituted or unsubstituted alkyl, cycloalkyl, alkylaryl or aryl. Preferably, M is Li or Mg, and X is Cl or I.

In one embodiment, M in compound (11) is Li (3-Py-Li). The reaction of compound (10) with 3-Py-Li is typically carried out in an organic solvent at a temperature of about −70° C. to 0° C., preferably at a temperature of about −60 to about −50° C., generally for about 15 min to about 1 day, or any period of time there between in the absence or presence of additives.

Suitable solvents for this step include, but are not limited to organic solvents such as ethers, e.g., diethyl ether, MTBE, diisopropyl ether, tetrahydrofuran (THF), 1,4-dioxane, 1,2-dimethoxyethane, petroleum ether, and 1,2-diethoxyethane; aliphatic and aromatic hydrocarbons such as hexane, cyclohexane, benzene, toluene, and xylene, and mixtures of these solvents. Each possibility represents a separate embodiment of the present invention. A currently preferred solvent is toluene. Another currently preferred solvent is THF.

The additive, if present, can be an amine, such as N,N'-tetramethylethylenediamine; amides, such as DMPU; inorganic salts, such as lithium chloride, lithium perchlorate, cadmium chloride, magnesium chloride, zinc chloride and ferric chloride; rare earth elements salts, such as lanthanide salts, preferably lathanium chloride or cerium chloride; or salt mixtures or complex salts, such as YCl$_3$.2LiCl, CeCl$_3$.2LiCl, NdCl$_3$.2LiCl, PrCl$_3$.2LiCl, DyCl$_3$.2LiCl and ErCl$_3$.2LiCl, preferably lithium chloride, zinc chloride, or LaCl$_3$.2LiCl. Each possibility represents a separate embodiment of the present invention.

In some embodiments, it was further found that an addition of additives to the reaction mixture can increase the yield, e.g., by improving the reaction intermediate stability, inhibiting the occurrence of side reactions at higher reaction temperatures and/or avoiding super-low temperature conditions.

In addition, it was found that the use of lanthanide salts can facilitate the reaction. Without wishing to be bound by any particular mechanism or theory, it is contemplated that this is achieved by any one or more of the following:

1). By improving 3-Py-Li solubility;
2). By activating the ketone in a Lewis-acid mode due to the oxophilic behavior of these salts;
3). Interaction of lanthanide salts with 3-Py-Li reduces the basic character of reagent (11) and therefore a deprotonation of alpha-acidic ketone (10) does not occur.

3-Py-Li is a commercially available compound or it can be prepared by well-known methods, described in Cai, D.; et al. *Tetrahedron Letters* (2002), 43 4285-4287; Grosi, P C et al. *Chem Commun (Camb)*. (2008) October 21; (39): 4813-5; and Neetu, R. et al. *Journal of Organometallic Chemistry* (2009), 694 2442-2447.

In another embodiment, M in compound (11) is MgX (3-Py-MgX) wherein X is a halogen such as Cl, Br or I. The reaction of compound (10) with 3-Py-MgX wherein X is Cl, Br or I is preferably carried out in an organic solvent at about room temperature (e.g., about 20° C. to 25° C.) to about reflux (which temperature will depend on the nature of the solvent), generally for about 0.1 hour to about 1 day, or any period of time there between, optionally in the presence of additives.

The nature of the solvent is not particularly limiting. Some examples include aromatic hydrocarbons such as benzene, toluene, and xylene; ethers such as diethyl ether, MTBE, diisopropyl ether, tetrahydrofuran (THF), 1,4-dioxane, 1,2-dimethoxyethane, and 1,2-diethoxyethane; and any mixtures thereof. Each possibility represents a separate embodiment of the present invention. THF is a currently preferred solvent. Another currently preferred solvent is toluene.

The additive can be selected from inorganic salts, such as lithium chloride, cadmium chloride, magnesium chloride, zinc chloride, rare earth elements salts, such as lanthanide salts, preferably lathanium chloride and cerium chloride or salt mixtures of any of the above.

Preferably, the additive, when used, is present at about 0.01 to 5.0 equivalents, and more preferably about 0.1-1.0 equivalents, relative to the amount of 3-Py-MgX.

Compound (12) can be isolated from the reaction mixture by adding water and a water-immiscible solvent, such as ethyl acetate, methylene chloride or toluene to the reaction mixture to obtain two phases, separating the organic layer, and evaporating the organic layer to obtain a residue. Evaporation can be carried out at an elevated temperature of about 45° C. to about 60° C. and/or a pressure of less than about one atmosphere. The crude product can be purified by any suitable technique, for example, by crystallization or through column chromatography or any other method known to a person of skill in the art. Alternatively, compound (12) can be used directly in the next step of the synthesis without purification.

acid, and the like. Also, polymeric acid resins and the like can be used. Each possibility represents a separate embodiment of the present invention.

Suitable solvents for use in this step include, but are not limited to ethers, such as diisopropyl ether, 1,4-dioxane, 1,2-dimethoxyethane, and 1,2-diethoxyethane; aliphatic and aromatic hydrocarbons such as hexane, petroleum ether, cyclohexane, benzene, toluene, and xylene, mixtures of these solvents. Each possibility represents a separate embodiment of the present invention. A preferred solvent is toluene and dioxane.

Under the conditions described, the removal of the acid-sensitive protecting group can take place. Temperature and reaction time are chosen in such a way as to prevent the formation of by-product (15) (Scheme 8).

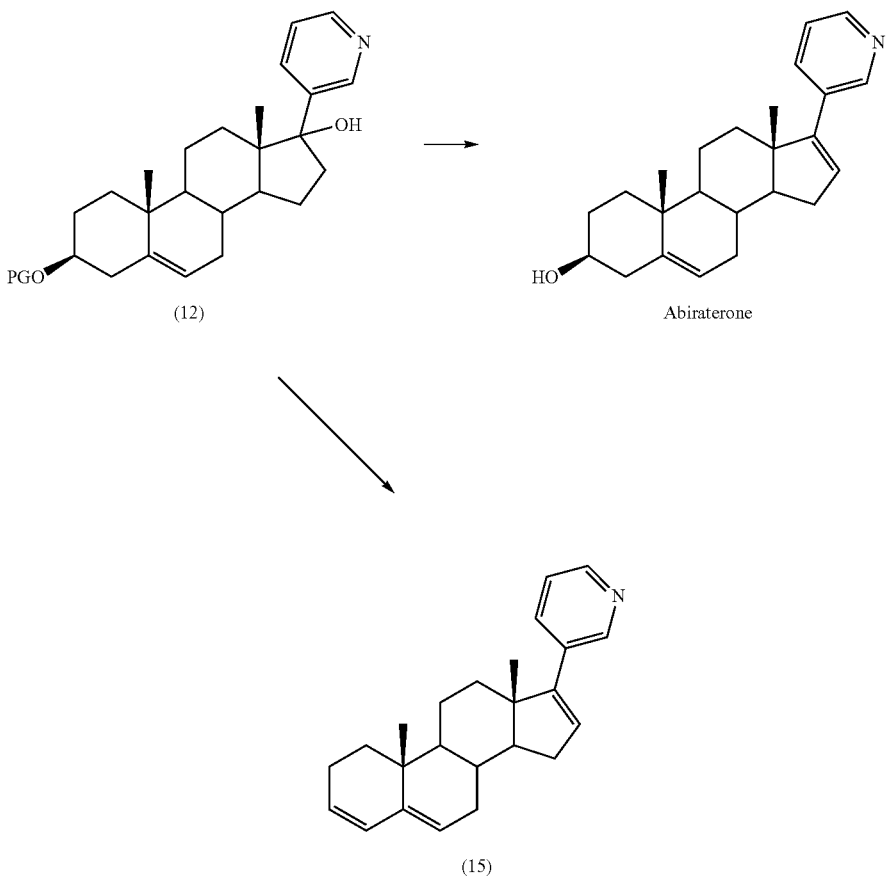

Scheme 8

Lathanide salts can be separated from the aqueous solution by any suitable method, described for example, in Morais, C. A. et al. *Hydrometallurgy*, (2004) 73 237-244, and can subsequently be recycled.

Step (b):

In step (b), conversion of alcohol (12) to compound (13) by a dehydration step may be carried out in the presence of a strong acid in an organic solvent at an elevated temperature of about 40° C. to about reflux. The acid can be an inorganic or organic acid such as hydrochloric, hydrobromic, phosphoric, sulfuric, para-toluenesulfonic, methanesulfonic or tungstic Alternatively, dehydration of compound (12) is carried out via formation of compound (14) (Scheme 6). Despite the fact that this adds an additional step in the process, the mild reaction conditions of such step prevent formation of undesirable impurities.

Step (c):

Finally, conversion of compound (13) to Abiraterone (16) and acetylation of Abiraterone (16) to Abiraterone acetate (1) and optionally purification of the final product can be performed according to known methods. This steps involves deprotection of the PG group to form the corresponding alcohol (16), followed by acetylation to form Abiraterone acetate (1) (Scheme 9):

Scheme 9

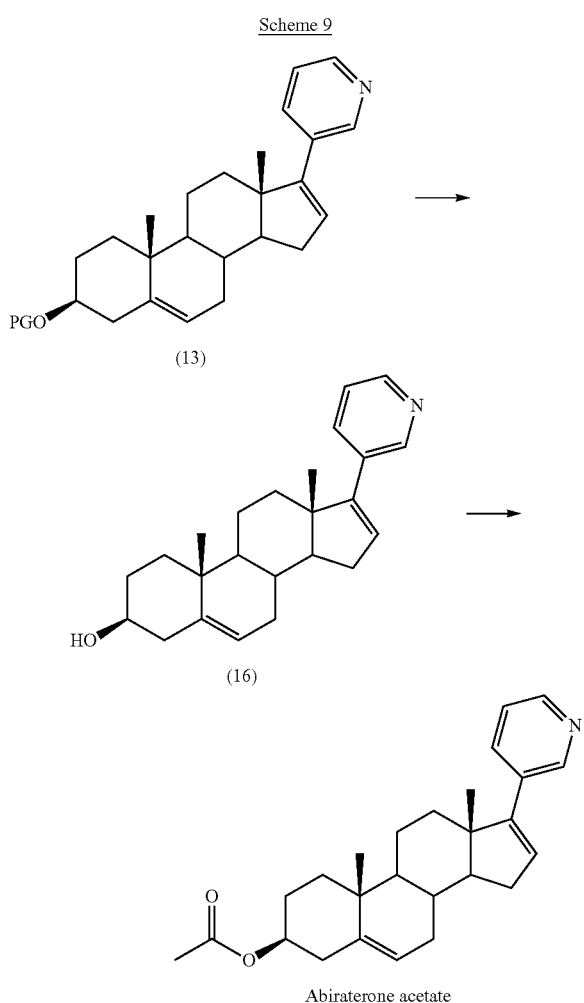

Deprotection of hydroxyl protecting group may be accomplished in-situ during step (b), e.g., when acidic conditions are used. Alternatively, deprotection may be carried out in accordance with methods known in the art, as described, e.g., in C. B. Reese and E. Haslam, "Protective Groups in Organic Chemistry," J. G. W. McOmie, Ed., Plenum Press, New York, N.Y., (1973), Chapters 3 and 4, respectively; T. W. Greene and P. G. M. Wuts, "Protective Groups in Organic Synthesis," 2nd ed., John Wiley and Sons, New York, N.Y., 1991, Chapters 2 and 3 pp. 473; and Kocienski, Philip J. Protecting Groups. 3rd Ed. (2005), pp. 679. For example, deprotection of silyl protection groups can be carried out using fluoride ion (F−), in particular tetrabutyl ammonium fluoride (TBAF).

Conversion of compound (16) to Abiraterone acetate can be accomplished by methods known in the art, by reacting compound (16) with an acetylating agent, e.g., acetyl chloride, acetic anhydride, methyl orthoformate or an equivalent acetylating agent.

In other embodiments, the present invention further relates to processes for converting Abiraterone acetate which is produced by the aforementioned process to its pharmaceutically acceptable salt. Such reaction can be carried out by methods well known in the art.

General Process

In some embodiments, the process of the present invention can be used to prepare compounds other than Abiraterone Acetate. Thus, a compound of formula (11) may be reacted with any ketone or aldehyde to form the corresponding alcohol, in a manner similar to that described for step (a) of the presently claimed process.

Thus, in one embodiment, the present invention relates to a general process for coupling ketones or aldehydes with a pyridinyl-metal derivative (11), comprising the step of reacting a ketone or aldehyde of the general formula (C) to a form pyridinyl-tertiary alcohol (A) (Scheme 7). This reaction may be carried out using the steps conditions and reagents as set forth for Step (a) above. The reaction is useful for coupling of compound (11) with any aldehyde or ketone to yield the corresponding tertiary alcohol.

Intermediates

In further embodiments, the present invention relates to novel compounds formed as intermediates in the processes of the present invention. One novel intermediate is a compound of general formula (12). In another embodiment, the present invention relates to an intermediate compound represented by the structure of formula (14). The structures of intermediates (12) and (14) are provided above.

EXAMPLES

Specific compounds which are representative of this invention were prepared as per the following examples and reaction sequences; the examples and the schemes depicting the reaction sequences are offered by way of illustration, to aid in the understanding of the invention and should not be construed to limit in any way the invention set forth in the claims which follow thereafter.

No attempt has been made to optimize the yields obtained in any of the reactions. Unless otherwise noted, the materials used in the examples were obtained from readily available commercial suppliers or synthesized by standard methods known to one skilled in the art of chemical synthesis.

Example 1

Preparation of Abiraterone

Preparation of Starting Materials:

Dehydroepiandrosterone and 3-bromopyridine are commercially available compounds.

Pyridine-3-yl lithium (3-Py-Li) was prepared according to Cai D.; et al. *Tetrahedron Letters* (2002), 43 4285-4287; Gros, P C et al. *Chem Commun (Camb).* (2008) October 21; (39):4813-5; and Neetu, R. et al. *Journal of Organometallic Chemistry* (2009), 694 2442-2447.

Pyridine-3-yl magnesium halide (3-Py-MgX) was prepared according to Paradies, H, H. et al., *Angew. Chem. Internat. Edit.* (1969), Vol. 8 No. 4, 279.

A solution of $LaCl_3 \cdot 2LiCl$ in THF was prepared according to EP 1759765.

A solution of $ZnCl_2$ (1 M) was prepared by drying $ZnCl_2$ (100 mmol, 136.3 g) in a Schlenk-flask under vacuum at 140° C. for 5 h. After cooling, 100 mL dry THF were added and stirring was continued until the salt was dissolved.

LiCl solution (0.5 M) was prepared by drying LiCl (100 mmol, 4.23 g) in a Schlenk-flask under vacuum at 140° C. for 5 h. After cooling, 200 mL dry THF were added and stirring was continued until the salt was dissolved.

Preparation of pyridine-3-ylmagnesium bromide—lithium chloride adduct

LiCl (5.30 g, 125 mmol) was heated under high vacuum for 20 min. Magnesium turnings (6.08 g, 250 mmol) and THF (250 mL) were added and the magnesium was activated with i-Bu$_2$AlH (0.14 mL, 114 mg, 0.8 mmol). After 5 min of stirring, the suspension was cooled to 0° C. and 3-bromopyridine (15.80 g, 100 mmol) was added slowly, so that the reaction temperature was kept below 10° C. After complete addition, the reaction mixture was stirred for an additional 30 min at 0° C. GC-analysis of a quenched reaction aliquot showed complete conversion. The yield of the magnesium reagent was determined by iodometric titration (266 mL, 0.34 M, 90.4 mmol, 90%).

Preparation of 3-(t-butyldimethylsiloxy) dehydroepiandrosterone (10, PG=SiMe$_2$t-Bu)

A solution of dehydroepiandrosterone (6 mmol) and imidazole (7 mmol) in 10 mL of DMF is treated under argon at room temperature with tert-butyldimethylchlorosilane (TB-DMS) (7 mmol). The reaction mixture is stirred at room temperature under TLC monitoring. After completion of the reaction, the mixture is diluted with ethyl acetate and washed with water and brine. The organic layer is dried over sodium sulfate, filtered and the solvent removed under reduced pressure. The crude residue can be purified by flash chromatography on silica gel (eluent: petroleum ether/ethylacetate 9/1) affording the expected compound in 84% yield. Alternatively, the crude product can be used in the next step without purification.

Preparation of Compound (12)

a) Using 3-Py-Li 3-(t-butyldimethylsiloxy) dehydroepiandrosterone (4.8 mmol) (10) in THF was added to the yellow slurry of 3-Py-Li (5 mmol) in toluene at −50° C. The mixture was stirred for 1 h at this temperature, then for 16 h at rt. The resulting mixture was quenched by saturated aqueous NH$_4$Cl, extracted with and washed by brine. The combined extracts were dried over MgSO$_4$. The organic phase was concentrated under reduced pressure and the resultant residue is a mixture (1:1) of starting compound (10) and product (12). This mixture can be purified by silica gel column chromatography (eluent: hexane/EtOAc), to give the desired product (12) with 48% yield and compound (10) for recycling.

Alternatively, the mixture of (10) and (12) can undergo the further transformations to Abiraterone and then purified by acid ion-exchange resin treatment. In this case dehydroepiandrosterone was removed from the resin by alcohol washing, and then Abiraterone was recovered by methanesulfonic acid treatment.

b) Using 3-Py-Li and LaCl$_3$.2LiCl

A solution of LaCl$_3$.2LiCl in THF (0.7 mmol, 0.3 equiv) was added to the yellow slurry of 3-Py-Li (2.1 mmol) in toluene at −20° C. and the mixture was allowed to stir at the same temperature for 1 h. Compound (10) (2.00 mmol) was then added neat and the resulting mixture was allowed to warm up to 25° C. and stirred at this temperature. The reaction conversion was monitored by TLC and HPLC analysis of reaction aliquots. After a complete conversion was reached, sat. aq. NH$_4$Cl and water were added. The aqueous layer was extracted with ethyl acetate, the combined extracts were dried (Na$_2$SO$_4$) and evaporated in vacuo and the crude residue was purified by flash column chromatography, yielding 75% of compound (12). Alternatively, the crude product can be used for the next step without purification.

c) Using 3-Py-MgCl

To 3-Py-MgCl (3 equiv.) (prepared according to the process described in WO 2009/070869 or Paradies, H, H. et al., *Angew. Chem. Internat. Edit.* (1969), Vol. 8 No. 4, 279) in dry THF was added solution of compound (10) (1 equiv.) in dry THF at 0° C. The mixture was stirred for 1 h at this temperature and for 16 h at rt. TLC has showed the presence of starting material. The reaction mixture was heated at reflux for 3 h. After workup LCMS showed 13% of desired product.

d) Using 3-Py-MgCl with ZnCl$_2$ and LiCl Additives

To pyridine-3-yl-magnesium chloride (3-Py-MgCl) (130 mmol) in 150 ml of THF was added ZnCl$_2$ (1.33 g, 10.0 mmol) and LiCl (5.49 g, 130 mmol) at room temperature under nitrogen atmosphere. This mixture was stirred at that temperature for 1 h. Then, compound (10) (100 mmol) was added at 0° C. The mixture was stirred at 0° C. for 5 h, and the reaction was monitored by TLC. The resulting mixture was quenched by saturated aqueous NH$_4$Cl (100 mL), extracted with EtOAc (100 mL×3), and washed with brine (100 mL). The combined extracts were dried over MgSO$_4$. The organic phase was concentrated under reduced pressure and the resultant residue was purified by silica gel column chromatography (eluent: hexane/EtOAc), to give the desired product (11) in 84% yield. Alternatively, the crude product can be used without purification in the next step.

Alternatively, compound (12) was prepared using pyridine-3-yl-magnesium bromide (3-Py-MgBr)—lithium chloride adduct and ZnCl$_2$.

Preparation of Abiraterone a) To a solution of compound (12) in dioxane was added conc. HCl and heated to reflux for 6 h. The reaction mixture was cooled to room temperature (RT) and diisopropylether was added. The organic phase was separated and washed with water. The aqueous phase and washings from the above workup step were extracted with hot toluene. The combined organic solutions were concentrated in vacuum and the residue was then dissolved in the minimum volume of hot methanol, and an equal volume of acetonitrile was added to the methanol solution. The acetonitrile/methanol solution was then concentrated to half its original volume on a rotary evaporator and the solution left to crystallize. The resultant white crystals were collected by filtration on a sinter, washed with cold acetonitrile and dried in vacuo to a constant weight (75%), mp 210-212° C. A second recrystallisation from toluene-methanol (50:1) afforded the product as white crystals (63%), mp 214-218° C.

b) via mesylate derivative (14, LG=MsO)

A solution of compound (0.1 mmol) (12) in dichloromethane (DCM) was cooled to 0° C. and a TEA (0.15 mmol) and MsCl (0.12 mmol) were added. The mixture was stirred for 2 h at rt. After workup the crude product was treated with TBAF in THF for 16 h. The mixture was worked up according to previous procedure (a) and yielded Abiraterone in 90% yield.

Example 2

Preparation of Abiraterone Acetate

Synthetic Scheme of Abiraterone Acetate:

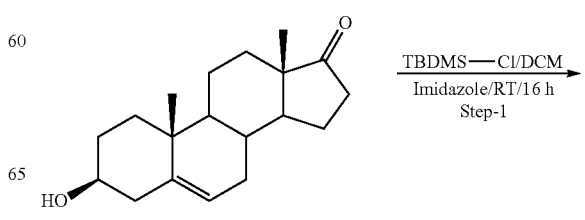

-continued

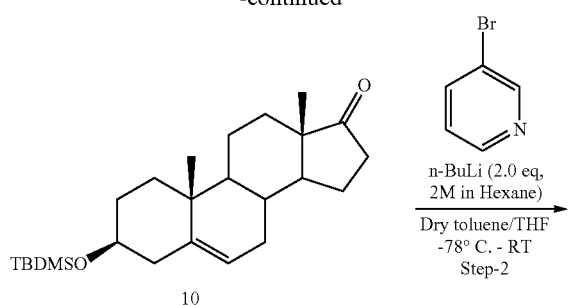

10

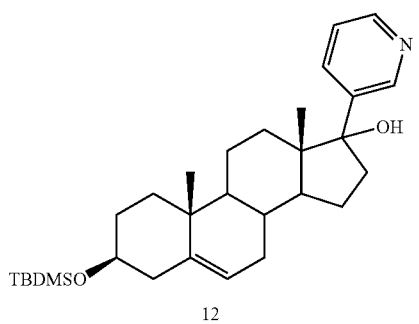

12

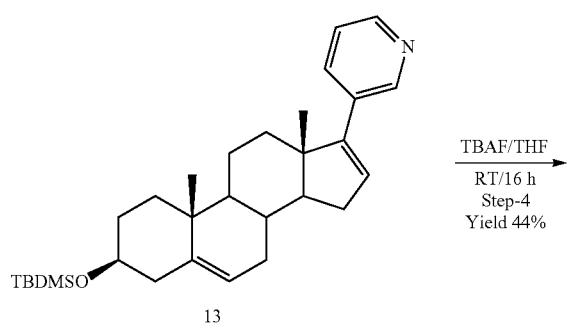

13

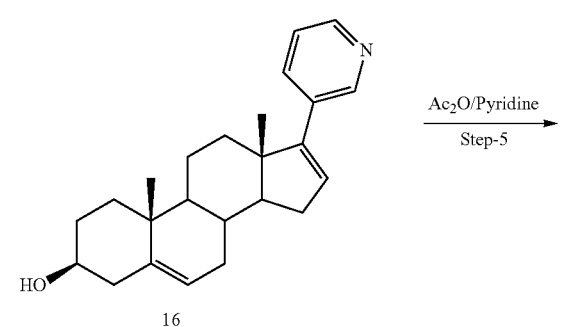

16

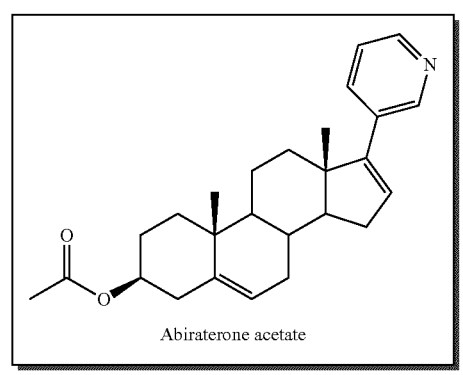

Abiraterone acetate

Reference: Surksik Moon et al. *Tetrahedron* (1990), vol 46, 7, 2287-2306.

Step 1: Synthesis of Compound-10:

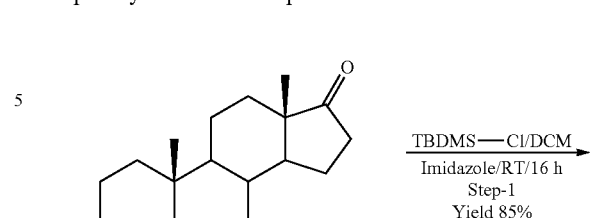

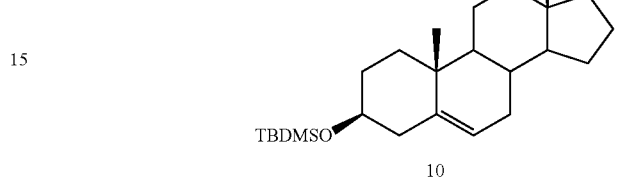

Procedure:

To a stirred solution of dehydroepiandrosterone (10 g, 34.67 mmol, 1 eq) and 1,3-imidazole (4.71 g, 69.34 mmol, 2 eq) in DCM (100 ml) was added TBDMS-Cl (10.4 g, 69.34 mmol, 2 eq). The reaction mixture was stirred for 16 h at RT & progress of the reaction was monitored by TLC.

Work-Up:

On completion of the reaction, the reaction mixture was quenched with water and extracted with ethyl acetate. The organic layer was dried over anhydrous $Na_2SO_4$ and concentrated under reduced pressure to obtain 12 g of crude (2) in 85% yield as a white solid. The product was confirmed by $^1$H NMR.

$^1$H NMR ($CDCl_3$, 400 MHz) δ: 5.36 (d, J=4.8 Hz, 1H), 3.45 (m, 1H), 2.43 (m, 4H), 2.0-2.35 (m, 1H), 1.9 (m, 1H), 1.8 (m, 2H), 1.7 (m, 2H), 1.4-1.65 (m, 5H), 1.2-1.39 (m, 2H), 0.95-1.15 (s, 6H), 0.8-0.9 (s, 11H), 0.05 s, 6H).

Step 2: Synthesis of Compound 12:

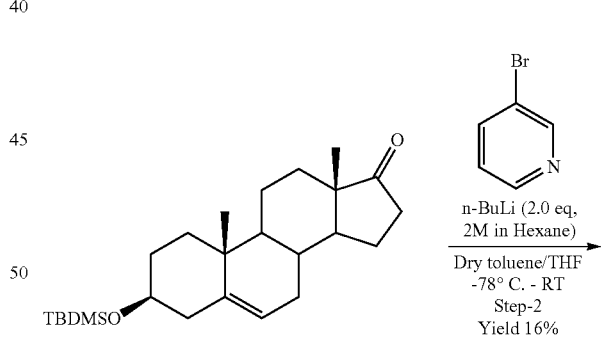

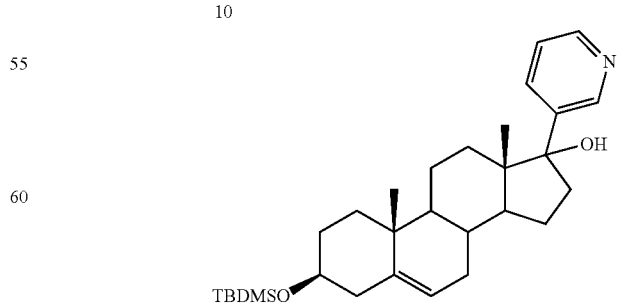

Procedure:

In a two necked RB flask 70 ml of dry toluene was added under argon atmosphere and cooled to −78° C. To this n-BuLi (2.5 M in hexane, 39.73 mL, 99.331 mmol, 2 eq) was added dropwise, followed by addition of 3-bromo pyridine (4.8 mL, 49.665 m·mol, 1 eq) in toluene solution (50 ml) dropwise over a 15 min at the same temperature. The reaction mixture was stirred additional for 30 min and a solution of (10) (20 g, 49.6 m·mol, 1 eq) in THF (100 mL) was added drop wise and stirred for 1 h at −78° C. Reaction mixture was allowed to room temperature and stirred for 16 h at same temperature. The reaction was monitored by TLC. TLC showed some new spots along with unreacted SM (~50%) & crude LCMS analysis showed ~16% of formation of desired product.

Work-Up:

The reaction mixture was quenched with $NH_4Cl$ solution at 0° C. and extracted with ethyl acetate. The organic layers were dried over anhydrous $Na_2SO_4$ and concentrated under reduced pressure to obtain the crude compound.

Purification:

The crude product was purified by column chromatography on silica gel column (100-200 mesh) in 3% methanol in DCM gradient and isolated 4 g of (3) in 16% yield as a yellow solid. The product was confirmed by $^1$H NMR and LCMS.

$^1$H NMR (CDCl$_3$, 400 MHz) δ: 8.7 (d, 1H), 8.55 (dd, 1H), 7.95 (dt, 1H), 7.5 (q, 1H), 5.22 (d, 1H), 3.4 (m, 1H), 2.4 (m, 4H), 2.1 (m, 1H), 1.8 (m, 1H), 1.7 (m, 2H), 1.6 (m, 2H), 1.4 (m, 5H), 1.2 (m, 2H), 1.1 (s, 6H), 0.8 (s, 11H), 0.05 (s, 6H).

Mass: m/z=482.42 (M+H)

Step-3: Synthesis of Compound 13:

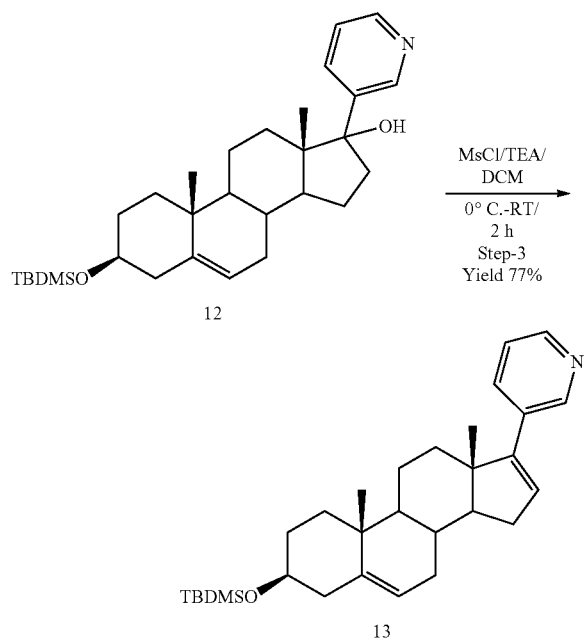

Procedure

To a stirred solution of (12) (8 g, 16.63 mmol, 1 eq) in DCM (80 ml) was added TEA (6.94 mL, 49.89 mmol, 3 eq) and methane sulfonyl chloride (3.86 mL, 49.89 mmol, 1 eq) drop wise at 0° C. and the reaction mixture was stirred for 3 h at room temperature. Reaction progress was monitored by TLC.

Work-Up:

On completion of the reaction, the reaction mixture was quenched with water and extracted with ethyl acetate, the organic layer was washed with brine and dried over $Na_2SO_4$ and concentrated under reduced pressure to obtain 6 g of crude (13) in 77% yield as a brown semisolid. The product was confirmed by $^1$H NMR and mass.

$^1$H NMR (CDCL$_3$, 400 MHz) δ: 8.75 (d, J=4.5, Hz, 1H), 8.61 (dd, J=8.02 Hz, 1H), 8.34 (dt, J=8.4 Hz, 1H), 7.81 (q, J=5.6 Hz, 1H), 6.37 (t, 1H), 5.22 (t, 1H), 3.45 (m, 1H), 2.3 (m, 4H), 2.3 (m, 1H), 1.9 (m, 1H), 1.6 (m, 2H), 1.5 (m, 2H), 1.2 (m, 5H), 1.3 (m, 2H), 1.2 (s, 6H), 0.9 (s, 11H), 0.05 (s, 6H).

Mass: m/z=464.49 [M+H]$^+$, 385.45 (fragment of pyridine)

Step-4: Synthesis of Abiraterone

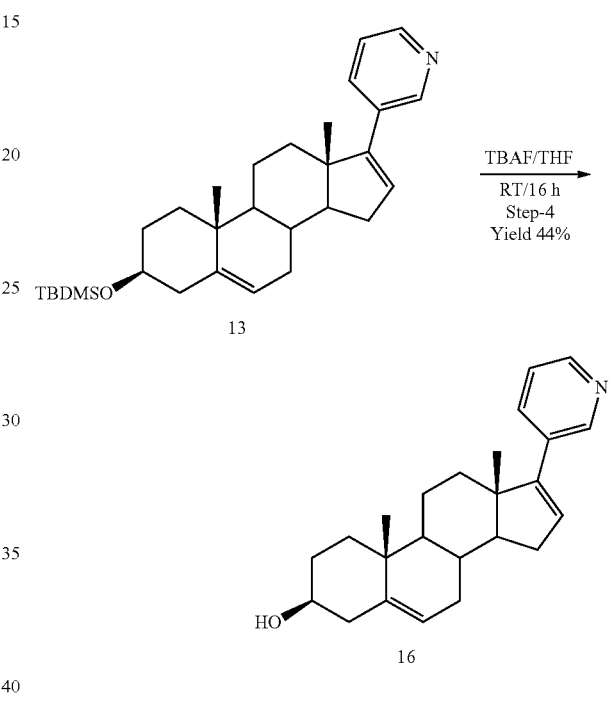

Procedure:

To a stirred solution of (13) (6 g, 12.95 mmol, 1 eq) in THF (20 ml) was added 40 mL of TBAF (1 M in THF). The reaction mixture was stirred for 16 h at room temperature. The progress of the reaction was monitored by TLC.

Work-Up:

On completion of the reaction, the reaction mixture was quenched with water and extracted with ethyl acetate, the organic layer was washed with brine and dried over anhydrous $Na_2SO_4$ and concentrated under reduced pressure to obtain crude (16).

Purification:

The crude compound was purified by column chromatography with 100-200 silica gel eluted with 3% methanol in DCM to furnished 2 g of the deprotected product (5) in 44% yield as a brown solid. The product was confirmed by $^1$H NMR and LCMS.

$^1$H NMR (CDCl$_3$, 400 MHz) δ: 8.62 (d, J=2 Hz, 1H), 8.45 (dd, J=1.2 Hz, 1H), 7.63 (dt J=2, Hz, 1H), 7.21 (q, J=11.6 Hz, 1H), 6.1 (q, J=2 Hz, 1H), 5.37 (t, J=2.4 Hz, 1H), 3.45 (m, 1H),), 2.3 (m, 4H), 2.3 (m, 1H), 1.9 (m, 1H), 1.6 (m, 2H), 1.5 (m, 2H), 1.2 (m, 5H), 1.3 (m, 2H), 1.2 (s, 6H).

Mass: m/z=350.34 [M+H]$^+$.

Step-5: Synthesis of Abiraterone Acetate:

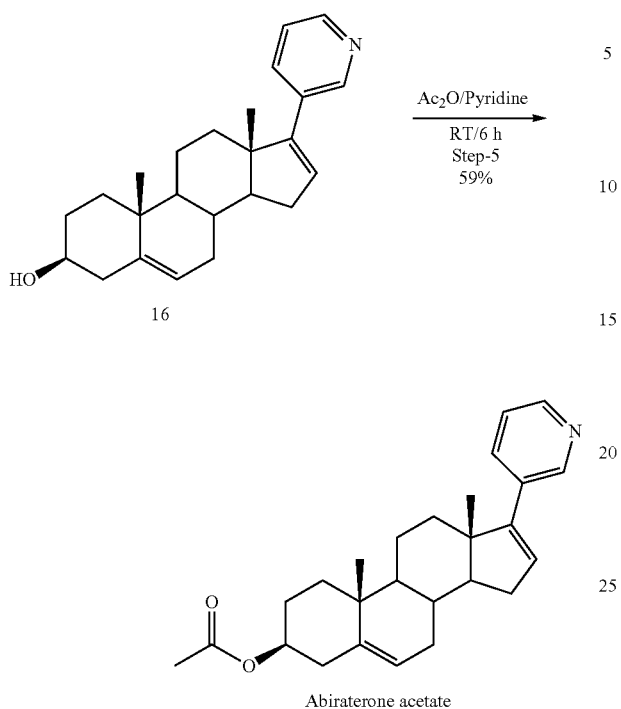

Procedure:

To a stirred solution of (16) (2.2 g, 6.307 mmol, 1 eq) in pyridine (80 ml) was added acetic anhydride (1.77 mL, 18.921 mmol, 3 eq) drop wise at 0° C., and the reaction mixture was stirred for 6 h at room temperature. Progress of the reaction mixture was monitored by TLC.

Work-Up:

On completion of the reaction, pyridine was distilled off and quenched with 1 N HCl solution and extracted with ethyl acetate. The organic layer was washed with brine and dried over anhydrous $Na_2SO_4$ and concentrated under reduced pressure to furnish crude product Abiraterone acetate.

Purification:

The crude compound was purified by column chromatography on silica gel (100-200 mesh) and eluted in 15% ethyl acetate in pet ether to furnished 1.45 g of Abiraterone acetate in 59% yield as an off white solid. Product was confirmed by $^1$H NMR, LCMS and FT-IR.

Melting Point: 147-149° C.

FT-IR (KBr): 3046.90 (C—H stretch), 2936.62, 2891.92, 2856.24, 1735.19 (C═O stretch) $cm^{-1}$.

$^1$H NMR (CDCl$_3$, 400 MHz) δ8.62 (d, J=1.2 Hz, 1H), 8.45 (dd, J=4.4 Hz, 1H), 7.63 (dt, J=7.6 Hz, 1H), 7.25 (q, J=4.4 Hz, 1H), 6.1 (s, 1H), 5.42 (d, J=5.2 Hz, 1H), 4.6 (m, 1H), 2.25-2.45 (m, 4H), 2.05 (m, 3H), 2.08 (m, 2H), 1.85 (m, 2H), 1.45-1.85 (m, 7H), 1.1-1.25 (m, 2H), 1.05 (s, 6H).

LCMS Purity:

99.55% [m/z=392.28 [M+H]$^+$, 433.31 (acetonitrile adduct)]

Mass:

m/z=392.28 (M+H), 433.31 (Acetonitrile adduct)

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A process for the preparation of (3β)17-(3-pyridinyl)androsta-5,16-dien-3-yl acetate represented by the structure of formula (1), and salts thereof the process comprising the steps of:

a) coupling a protected dehydroepiandrosterone (10) with a pyridinyl derivative (11) to form a pyridinyl hydroxy derivative (12):

wherein

PG is a hydroxyl protecting group; and

M is selected from the group consisting of Li, Na, K, MgX, ZnX, CdX, Si(R)$_3$, Ge(R)$_3$ and Sn(R$_3$); wherein X is a halogen and R is a substituted or unsubstituted alkyl, cycloalkyl, alkylaryl or aryl;

b) converting compound (12) to (17-pyridin-3-yl)-androsta-5,16-diene (13):

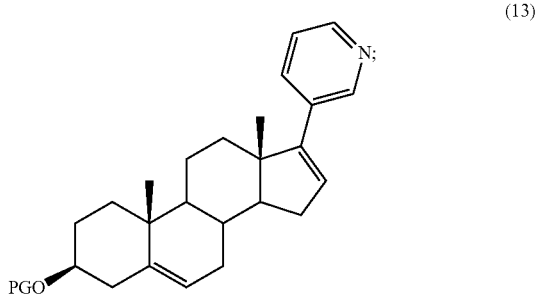

and c) transforming compound (13) into (3β)-17-(pyridin-3-yl) androsta-5,16-dien-3-ol (Abiraterone acetate) (1).

2. The process according to claim 1, wherein the hydroxyl protecting group PG is selected from the group consisting of acetate (Ac), benzyl (Bzl), Si($R^a$)$_3$, tetrahydropyranyl (THP) and trityl (Trt), wherein $R^a$ is a substituted or unsubstituted alkyl, cycloalkyl, alkylaryl or aryl.

3. The process according to claim 1, wherein M is Li or MgX, wherein X is Cl, Br or I.

4. The process according to claim 1, wherein step (a) is carried out by reacting compound (10) with 3-Py-Li in an organic solvent at a temperature of about −70° C. to about 0° C., in the absence or presence of one or more additives.

5. The process according to claim 4, wherein step (a) is carried out in the presence of an additive selected from the group consisting of: (i) an amine; (ii) an amide; (iii) an inorganic salt; (iv) a rare earth element salt; and (v) salt mixtures or complex salts.

6. The process according to claim 5, wherein
(i) the amine is N,N'-tetramethylethylenediamine;
(ii) the amide is 1,3-Dimethyl-3,4,5,6-tetrahydro-2(1H)-pyrimidinone (DMPU);
(iii) the inorganic salt is selected from lithium chloride, lithium perchlorate, cadmium chloride, magnesium chloride, zinc chloride and ferric chloride;
(iv) the rare earth element salt is a lanthanide salt selected from lathanium chloride and cerium chloride;
(v) the salt mixtures of complex salts are selected from YCl$_3$.2LiCl, CeCl$_3$.2LiCl, NdCl$_3$.2LiCl, PrCl$_3$.2LiCl, DyCl$_3$.2LiCl and ErCl$_3$.2LiCl.

7. The process according to claim 6, wherein the additive is lithium chloride, zinc chloride, or LaCl$_3$.2LiCl.

8. The process according to claim 1, wherein step (a) is carried out by reacting compound (10) with 3-Py-MgX in an organic solvent at about room temperature to about reflux in the absence or presence of an additive.

9. The process according to claim 8, wherein step (a) is carried out in the presence of an additive selected from the group consisting of: lithium chloride, cadmium chloride, magnesium chloride, zinc chloride, a rare earth element salt, and salt mixtures of any of said additives.

10. The process according to claim 9, wherein the additive is present from about 0.01 to about 5.0 equivalents relative to the 3-Py-MgX.

11. The process according to claim 1, wherein step (b) is carried out in the presence of a strong acid in an organic solvent at an elevated temperature of about 40° C. to about reflux.

12. The process according to claim 11, wherein the acid is an inorganic or organic acid selected from the group consisting of hydrochloric acid, hydrobromic acid, phosphoric acid, sulfuric acid, para-toluenesulfonic acid, methanesulfonic acid, tungstic acid, and polymeric acid resins.

13. The process according to claim 1, wherein step (b) is carried out by conversion of compound (12) to (13) directly.

14. The process according to claim 1, wherein step (b) is carried out by conversion of the hydroxyl in compound (12) to a leaving group to generate compound (14), followed by converting compound (14) to compound (13):

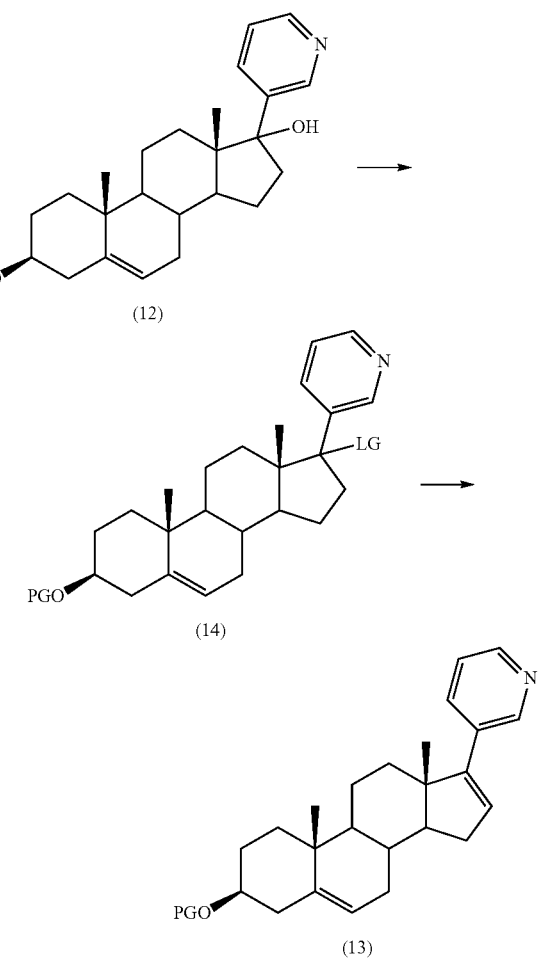

wherein LG is a leaving group selected from a halogen or a sulfonate ester group of the formula —OSO$_2$R$^b$ wherein R$^b$ is a substituted or unsubstituted alkyl, cycloalkyl, alkylaryl or aryl.

15. The process according to claim 1, further comprising the step of converting Abiraterone acetate into a salt thereof with a pharmaceutically acceptable acid.

16. A compound represented by the structure of formula (12), or a salt thereof:

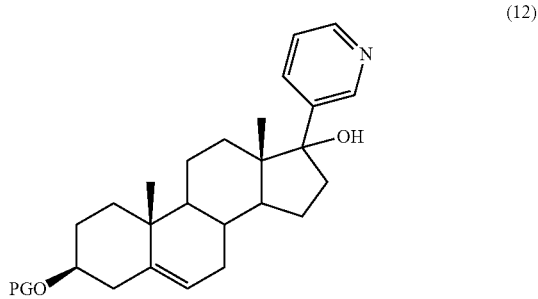

wherein PG is a hydroxyl protecting group.

17. A compound represented by the structure of formula (14):

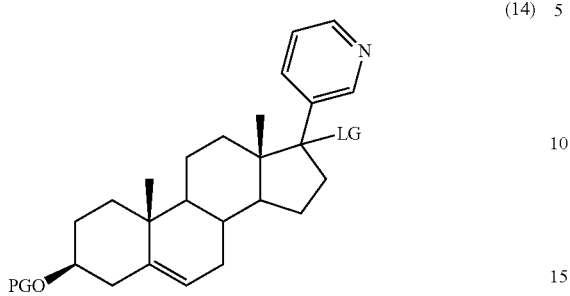

(14)

wherein
PG is a hydroxyl protecting group; and
LG is a leaving group selected from a halogen or a sulfonate ester group of the formula
—OSO$_2$R$^b$ wherein R$^b$ is a substituted or unsubstituted alkyl, cycloalkyl, alkylaryl or aryl.

18. The compound according to claim 17, wherein the hydroxyl protecting group PG is selected from the group consisting of acetate (Ac), benzyl (Bzl), Si(R$^a$)$_3$, tetrahydropyranyl (THP) and trityl (Trt), wherein R$^a$ is a substituted or unsubstituted alkyl, cycloalkyl, alkylaryl or aryl.

* * * * *